(12) United States Patent
Akita et al.

(10) Patent No.: US 12,399,233 B2
(45) Date of Patent: Aug. 26, 2025

(54) MAGNETIC SENSOR AND BIOMAGNETISM MEASURING APPARATUS

(71) Applicants: NATIONAL INSTITUTE OF ADVANCED INDUSTRIAL SCIENCE AND TECHNOLOGY, Tokyo (JP); AICHI STEEL CORPORATION, Aichi (JP)

(72) Inventors: Ippei Akita, Ibaraki (JP); Michiharu Yamamoto, Aichi (JP); Hitoshi Aoyama, Aichi (JP); Takeshi Kawano, Aichi (JP)

(73) Assignees: NATIONAL INSTITUTE OF ADVANCED INDUSTRIAL SCIENCE AND TECHNOLOGY (JP); AICHI STEEL CORPORATION (JP)

( * ) Notice: Subject to any disclaimer, the term of this patent is extended or adjusted under 35 U.S.C. 154(b) by 146 days.

(21) Appl. No.: 18/258,130

(22) PCT Filed: Dec. 21, 2021

(86) PCT No.: PCT/JP2021/047421
§ 371 (c)(1),
(2) Date: Jun. 16, 2023

(87) PCT Pub. No.: WO2022/138671
PCT Pub. Date: Jun. 30, 2022

(65) Prior Publication Data
US 2024/0110998 A1     Apr. 4, 2024

(30) Foreign Application Priority Data
Dec. 23, 2020 (JP) .................... 2020-214192

(51) Int. Cl.
*G01R 33/00* (2006.01)
*A61B 5/242* (2021.01)

(52) U.S. Cl.
CPC .......... *G01R 33/0029* (2013.01); *A61B 5/242* (2021.01)

(58) Field of Classification Search
CPC .......................... G01R 33/0029; A61B 5/242
See application file for complete search history.

(56) References Cited

U.S. PATENT DOCUMENTS

| 2010/0103015 A1 | 4/2010 | Yoshida et al. |
| 2014/0184214 A1 | 7/2014 | Schäffer et al. ............ 324/253 |

(Continued)

FOREIGN PATENT DOCUMENTS

| JP | 2010-098668 A | 4/2010 |
| JP | 2016-057190 A | 4/2016 |

(Continued)

OTHER PUBLICATIONS

Luigi Rovati et al.: "Zero-Field Readout Electronics for Planar Fluxgate Sensors Without Compensation Coil", IEEE Transactions on Industrial Electronics, IEEE Service Center, Piscataway, NJ, USA, vol. 59, No. 1, Jan. 1, 2012 (Jan. 1, 2012), pp. 571-578, XP011478671, ISSN: 0278-0046, DOI: 10.1109/TIE.2011. 2134055.

(Continued)

*Primary Examiner* — Feba Pothen
(74) *Attorney, Agent, or Firm* — OSTROLENK FABER LLP

(57) ABSTRACT

A magnetic sensor includes: a sensor head having a magnetic material; a drive unit configured to energize the sensor head; a pickup coil close to the sensor head; and an information processing unit configured to generate a bias magnetic field by energizing the pickup coil and detect a signal (Continued)

corresponding to an induced voltage generated in the pickup coil, in which the information processing unit generates a difference signal indicating a difference between a first signal corresponding to a first voltage generated in the pickup coil when the sensor head is in an energized state and a second signal corresponding to a second voltage generated in the pickup coil when the sensor head is in a non-energized state.

11 Claims, 6 Drawing Sheets

(56) References Cited

U.S. PATENT DOCUMENTS

| | | |
|---|---|---|
| 2017/0234938 A1 | 8/2017 | Nagao et al. |
| 2018/0120357 A1 | 5/2018 | Takenaka |
| 2020/0256930 A1 | 8/2020 | Hinshaw |
| 2021/0025959 A1 | 1/2021 | Yamamoto et al. |

FOREIGN PATENT DOCUMENTS

| | | | |
|---|---|---|---|
| JP | 5924503 B | | 5/2016 |
| JP | 2016191642 A | * | 11/2016 |
| JP | 2017-211258 A | | 11/2017 |
| JP | 2019-010483 A | | 1/2019 |
| JP | 2019-012045 A | | 1/2019 |
| JP | 2019-184240 A | | 10/2019 |
| JP | 2019-184473 A | | 10/2019 |

OTHER PUBLICATIONS

International Search Report mailed Feb. 22, 2022 in corresponding PCT International Application No. PCT/JP2021/047421.

* cited by examiner

MAGNETIC SENSOR AND BIOMAGNETISM MEASURING APPARATUS

CROSS-REFERENCE TO RELATED APPLICATIONS

The present application is a 35 U.S.C. §§ 371 national stage application of International Application No. PCT/JP2021/047421 filed Dec. 21, 2021, which claims priority to Japanese Patent Application No. 2020-214192, filed Dec. 23, 2020, the contents of which are incorporated herein by reference.

TECHNICAL FIELD

The present invention relates to a magnetic sensor and a biomagnetic measurement device.

BACKGROUND ART

A magnetic sensor is known which detects an induced voltage corresponding to an external magnetic field, which is induced in a pickup coil by energizing an amorphous wire around which the pickup coil is wound.

In this type of magnetic sensor, in order to suppress sensitivity variations caused by environmental changes such as temperature, manufacturing variations, and the like, a predetermined magnetic field (hereinafter referred to as a "bias magnetic field") is generated in the amorphous wire to offset the variation in sensitivity. Here, in order to generate a bias magnetic field, a separate coil for generating the bias magnetic field is required in addition to the pickup coil, which increases the cost. Therefore, Patent Document 1 discloses that a single pickup coil detects an induced voltage and generates a bias magnetic field by generating the bias magnetic field with the pickup coil.

CITATION LIST

Patent Documents

Patent Document 1

Japanese Patent No. 5924503

SUMMARY OF INVENTION

Technical Problem

However, since the pickup coil has a parasitic series resistance, when the pickup coil is energized to generate a bias magnetic field, a voltage due to the influence of the parasitic series resistance is generated in the pickup coil in addition to the induced voltage corresponding to the external magnetic field. Therefore, when the voltage generated in the pickup coil is detected, a mixed voltage of the induced voltage corresponding to the external magnetic field and the voltage due to the influence of the parasitic series resistance is detected, and the induced voltage corresponding to the external magnetic field cannot be accurately detected, in some cases.

The present invention has been made in view of such circumstances, and an object of the present invention is to provide a magnetic sensor and a biomagnetic measurement device capable of accurately detecting an induced voltage corresponding to an external magnetic field when detecting an induced voltage and generating a bias magnetic field with one pickup coil.

Solution to Problem (1) According to an aspect of the present invention, there is provided a magnetic sensor including: a sensor head having a magnetic material; a drive unit configured to energize the sensor head; a pickup coil close to the sensor head; and an information processing unit configured to generate a bias magnetic field by energizing the pickup coil and detect a signal corresponding to an induced voltage generated in the pickup coil, in which the information processing unit generates a difference signal indicating a difference between a first signal corresponding to a first voltage generated in the pickup coil when the sensor head is in an energized state and a second signal corresponding to a second voltage generated in the pickup coil when the sensor head is in a non-energized state.

(2) In the magnetic sensor according to (1) above, the information processing unit may include an amplifier circuit, detect a third signal corresponding to a voltage generated at an input terminal using an effect of a virtual ground of the input terminal of the amplifier circuit, generate a fourth signal by subtracting the second signal and the third signal from the first signal, and amplify the fourth signal with the amplifier circuit.

(3) In the magnetic sensor according to (2) above, the information processing unit may include a first measurement unit that detects the first signal in the energized state, detects the second signal in the non-energized state, and generates the difference signal indicating a difference between the first signal and the second signal, and a second measurement unit that feeds back a current corresponding to an output signal of the amplifier circuit to the pickup coil, detects the third signal in the non-energized state, and generates the fourth signal indicating a difference between the difference signal and the third signal.

(4) In the magnetic sensor according to (3) above, the information processing unit may further include a switch that cuts off electrical connection between the first measurement unit and the second measurement unit when the first measurement unit detects the first signal.

(5) In the magnetic sensor according to (1) above, the information processing unit may include an amplifier circuit that amplifies the voltage generated in the pickup coil, an AD converter that converts an output signal from the amplifier circuit into a digital signal, a measurement unit that detects a first digital signal output from the AD converter in the energized state and a second digital signal output from the AD converter in the non-energized state and generates the difference signal indicating a difference between the first digital signal and the second digital signal, and a DA converter that converts the difference signal calculated by the measurement unit into an analog signal and feeds back the analog signal to the pickup coil.

(6) In the magnetic sensor according to any one of (1) to (5) above, the sensor head may be an amorphous wire.

(7) According to another aspect of the present invention, there is provided a biomagnetic measurement device including: the magnetic sensor according to any one of claims 1 to 6; and a biomagnetic measurement unit configured to measure magnetism emitted by a living body using an output signal from the magnetic sensor.

Advantageous Effects of Invention

As described above, according to the present invention, it is possible to accurately detect an induced voltage corresponding to an external magnetic field when detecting an induced voltage and generating a bias magnetic field with one pickup coil.

DESCRIPTION OF EMBODIMENTS

Figure 1:
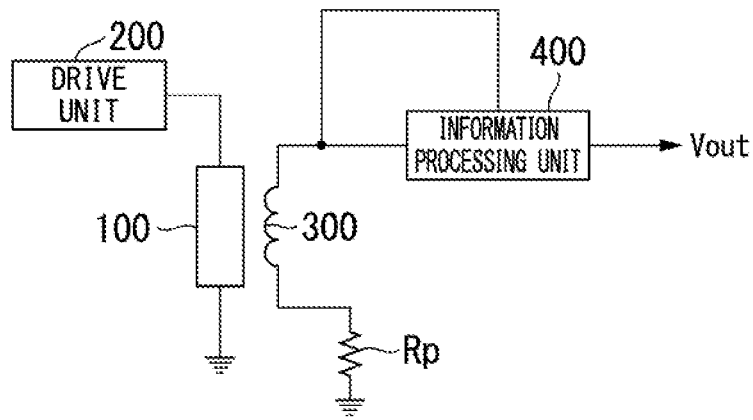
FIG. 1 is a diagram showing an example of a basic configuration of a magnetic sensor according to a first embodiment.

The present invention will be described below through embodiments of the invention, but the following embodiments do not limit the invention according to the claims. Further, not all combinations of features described in the embodiments are essential for the solution of the invention. Note that, in the drawings, the same or similar parts may be denoted by the same reference numerals, and duplicate description may be omitted. In addition, the shapes and sizes of elements in the drawings may be exaggerated for clearer description.

The "connection" described below is electrical connection. Electrical connection means that power or electrical signals can be transferred directly or indirectly. Electrical connection may be connection via components such as cables, resistors, capacitors, diodes, circuit breakers, and the like.

First Embodiment

FIG. 1 is a diagram showing an example of a basic configuration of a magnetic sensor 1 according to a first embodiment. As shown in FIG. 1, the magnetic sensor 1 includes a sensor head 100, a drive unit 200, a pickup coil 300, and an information processing unit 400.

The sensor head 100 includes magnetic material. Examples of the sensor head 100 include a magneto-impedance element, a fluxgate sensor, a magnetic core, and the like. When the sensor head 100 is a magneto-impedance element, the magneto-impedance element is an element whose impedance changes with an external magnetic field, and is, for example, an amorphous wire.

The drive unit 200 energizes the sensor head 100. For example, the drive unit 200 energizes the sensor head 100 by outputting a pulse current or a high frequency current. A state in which the drive unit 200 energizes the sensor head 100 is referred to as an "energized state", and a state in which the drive unit 200 does not energize the sensor head 100 is referred to as a "non-energized state".

The pickup coil 300 is disposed close to the sensor head 100. Specifically, the pickup coil 300 is disposed close to the sensor head 100 so that an induced voltage proportional to the external magnetic field is generated in the pickup coil 300 in an energized state. For example, the pickup coil 300 is wound around the sensor head 100. Note that the pickup coil 300 has a parasitic series resistance Rp.

The information processing unit 400 is connected to the pickup coil 300. The information processing unit 400 energizes the pickup coil 300 to generate a bias magnetic field. The method of energizing the pickup coil 300 to generate the bias magnetic field is not particularly limited.

The information processing unit 400 detects a signal corresponding to the voltage generated in the pickup coil 300. Here, the signal corresponding to the voltage generated in the pickup coil 300 may be a signal of the voltage itself, may be a signal generated based on the voltage, or may be a signal obtained by subjecting the voltage to predetermined signal processing such as amplification, filtering, and AD conversion. In this way, the magnetic sensor 1 uses a single pickup coil 300 to detect the voltage generated in the pickup coil 300 and generate the bias magnetic field.

The information processing unit 400 detects a first signal, which is a signal corresponding to the voltage (hereinafter referred to as a "first voltage") generated in the pickup coil 300 in the energized state. Also, the information processing unit 400 detects a second signal, which is a signal corresponding to the voltage (hereinafter referred to as "second voltage") generated in the pickup coil 300 in the non-energized state. The information processing unit 400 then generates a difference signal indicating a difference between the first signal and the second signal. The information processing unit 400 generates an output signal Vout by amplifying the difference signal. The order of detection of the first signal and detection of the second signal by the information processing unit 400 is not particularly limited. The information processing unit 400 may detect the second signal after detecting the first signal, or may detect the first signal after detecting the second signal.

As an example, the information processing unit 400 of the present embodiment feeds back a current corresponding to the output signal Vout to the pickup coil 300 to energize the pickup coil 300 and generate a bias magnetic field.

Figure 2:
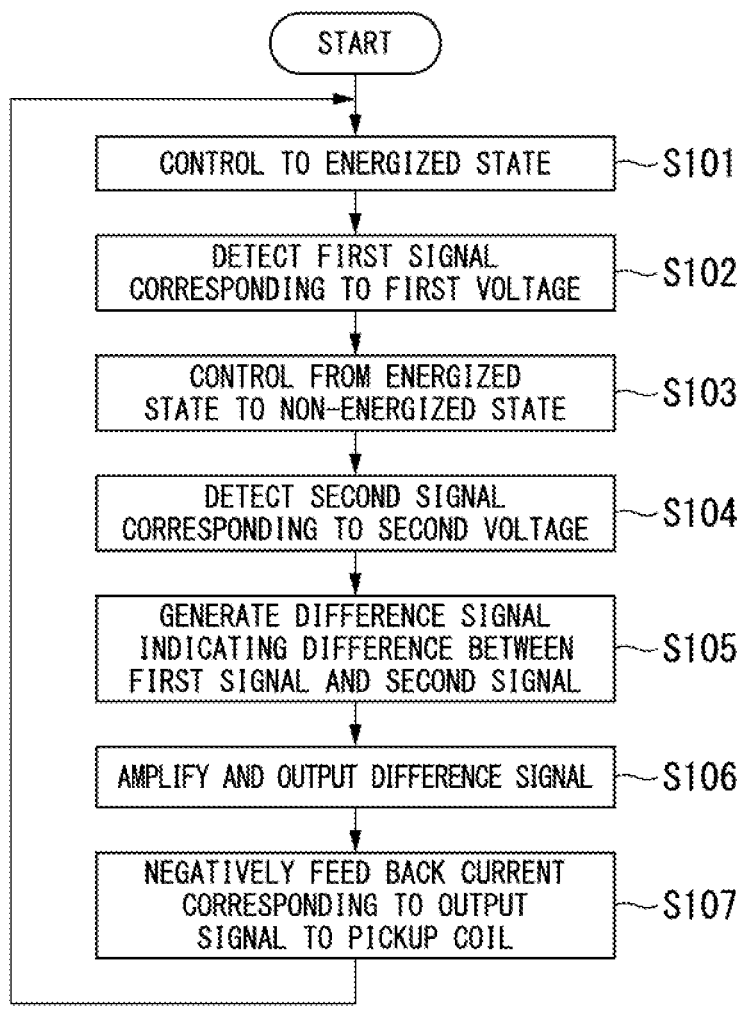
FIG. 2 is a flowchart of operation of the magnetic sensor according to the first embodiment.

The flow of operation of the magnetic sensor 1 will be described below. FIG. 2 is a flowchart of the operation of the magnetic sensor 1.

The magnetic sensor 1 controls the sensor head 100 to be in an energized state by energizing the sensor head 100 (step S101). The information processing unit 400 detects a first signal corresponding to a first voltage generated in the pickup coil 300 in the energized state (step S102).

Here, when the sensor head 100 is energized, a high frequency induced voltage (hereinafter referred to as a "high frequency voltage") corresponding to the external magnetic field is generated in the pickup coil 300. However, the pickup coil 300 is always energized to generate a bias magnetic field, and due to the influence of the parasitic series resistance Rp of the pickup coil 300, a voltage having a frequency lower than that of the high frequency voltage (hereinafter referred to as a "low frequency voltage") is also generated in the pickup coil 300 at the same time. For example, the low frequency voltage is a dynamic offset voltage due to the parasitic series resistance Rp. Therefore, the first voltage generated in the pickup coil 300 in the energized state is a voltage in which at least the high frequency voltage and the low frequency voltage are mixed.

When the magnetic sensor 1 detects the first signal, the magnetic sensor 1 controls the sensor head 100 to be in a non-energized state by stopping the energization to the sensor head 100 (step S103). The information processing unit 400 detects a second signal corresponding to a second voltage generated in the pickup coil 300 in the non-energized state (step S104). In the example shown in FIG. 2, the processes are performed in the order of steps S101, S102, S103, S104, and S105, but the present invention is not limited thereto, and the processes may be performed in the order of steps S103, S104, S101, S102, and S105.

Here, when the energization to the sensor head 100 is stopped, the high frequency voltage disappears, and thus only the low frequency voltage is generated in the pickup coil 300. Therefore, the second voltage generated in the pickup coil 300 in the non-energized state does not include at least the high frequency voltage, but includes the low frequency voltage due to the parasitic series resistance Rp.

Therefore, the information processing unit 400 obtains the difference between the first signal and the second signal to generate a difference signal, thereby extracting only the high frequency voltage signal (difference signal) corresponding to the external magnetic field (step S105). Here, since the difference signal is a minute signal, the information processing unit 400 amplifies the difference signal and outputs the output signal Vout, which is an amplified signal, to the outside (step S106). Further, the information processing unit 400 negatively feeds back a signal corresponding to the output signal Vout to the pickup coil 300 (step S107).

As described above, the magnetic sensor 1 according to the first embodiment samples the signal corresponding to the voltage generated in the pickup coil 300 in each of the energized state and the non-energized state, and obtains a difference between the two sampled signals. Thereby, it is possible to accurately detect an induced voltage (high frequency voltage) corresponding to an external magnetic field when detecting an induced voltage and generating a bias magnetic field with one pickup coil. In addition, since the magnetic sensor 1 can accurately detect the induced voltage corresponding to the external magnetic field, it is possible to negatively feed back the current corresponding to the induced voltage corresponding to the external magnetic field instead of the first voltage and it is possible to suppress the deterioration of the negative feedback effect due to the influence of the parasitic series resistance.

Here, since the first voltage is a voltage in which a high frequency voltage and a low frequency voltage are mixed, a method of extracting only the high frequency voltage from the first voltage using a high-pass filter is also conceivable. However, in this method, the resistive element forming the high-pass filter may become a noise source, degrading the sensitivity of the magnetic sensor 1. In addition, the value of the capacitive element forming the high-pass filter is large, which is unsuitable for integration of CMOS and the like. In the present embodiment, only the high frequency voltage can be extracted from the first voltage without using a high-pass filter, which is suitable for integration of CMOS and the like.

Here, when the magnetic sensor 1 according to the first embodiment includes an amplifier circuit such as an operational amplifier that amplifies the difference signal, low frequency noise components such as 1/f noise of the amplifier circuit and offset voltage caused by manufacturing variations may be detected as a third signal, and the difference between the third signal and the first signal may be obtained. For example, the information processing unit 400 subtracts the second signal and the third signal from the first signal to generate a fourth signal with reduced low frequency noise components, thereby more accurately detecting an induced voltage (high frequency voltage) corresponding to the external magnetic field). In this case, the information processing unit 400 generates the output signal Vout by amplifying the fourth signal with the amplifier circuit. The timing at which the information processing unit 400 detects the third signal is not particularly limited, but for example, the third signal is detected in the non-energized state. Further, the information processing unit 400 may obtain a difference signal indicating the difference between the first signal and the second signal and obtain the difference between the difference signal and the third signal to generate the fourth signal, or simultaneously subtract the second signal and the third signal from the first signal. Further, the information processing unit 400 may obtain the difference between the first signal and the third signal, and obtain the difference between the difference signal and the second signal to generate the fourth signal.

Second Embodiment

In a second embodiment, a specific first configuration example of the information processing unit 400 of the first embodiment will be described. However, the configuration of the information processing unit 400 of the first embodiment is not limited to the specific configuration described in the second embodiment. In the following description, portions having functions similar to those described in the first embodiment will be given the same names and reference numerals, and detailed descriptions of the functions will be omitted. However, for convenience of description, the magnetic sensor of the second embodiment is called a "magnetic sensor 1A", and the information processing unit 400 of the second embodiment is called an "information processing unit 400A".

Figure 3:
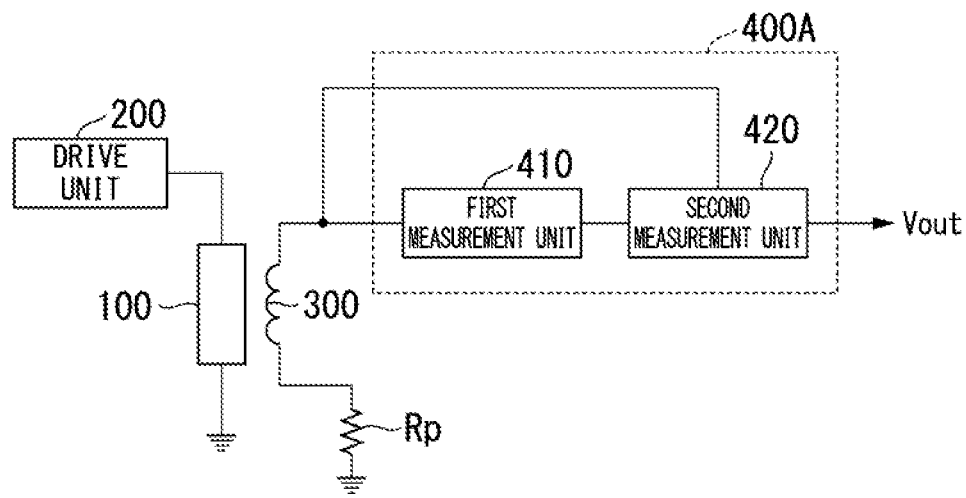
FIG. 3 is a diagram showing a configuration example of a magnetic sensor according to a second embodiment.

FIG. 3 is a diagram showing a configuration example of a magnetic sensor 1A according to the second embodiment. The magnetic sensor 1A includes a sensor head 100, a drive unit 200, a pickup coil 300, and an information processing unit 400A.

The information processing unit 400A includes a first measurement unit 410 and a second measurement unit 420.

The first measurement unit 410 detects a first signal in the energized state, detects a second signal in the non-energized state, and generates a difference signal indicating a difference between the first signal and the second signal.

Figure 4:
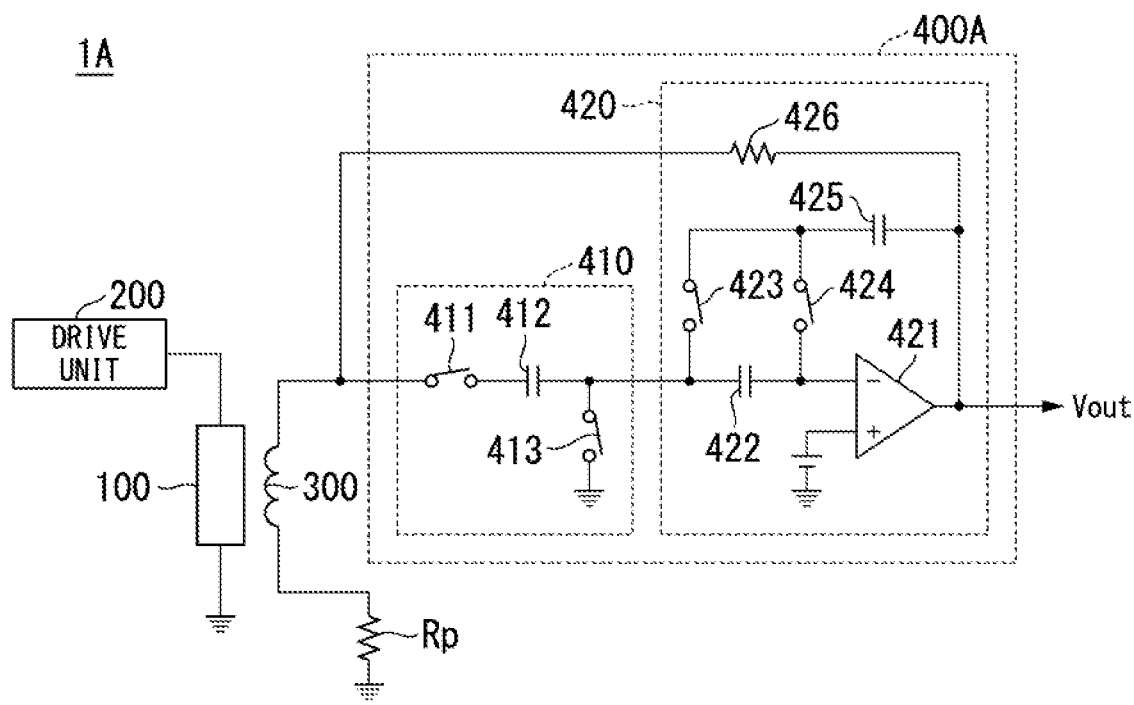
FIG. 4 is a schematic configuration diagram of a first measurement unit and a second measurement unit according to the second embodiment.

The second measurement unit 420 is connected to the first measurement unit 410. The second measurement unit 420 has an amplifier circuit and feeds back a current corresponding to an output signal Vout of the amplifier circuit to the pickup coil 300. In addition, the second measurement unit 420 detects a third signal in the non-energized state, and generates a fourth signal indicating a difference between the difference signal output from the first measurement unit 410 and the third signal. The configurations of the first measurement unit 410 and the second measurement unit 420 will be described below with reference to FIG. 4. FIG. 4 is a schematic configuration diagram of the first measurement unit 410 and the second measurement unit 420.

As shown in FIG. 4, the first measurement unit 410 includes a switch 411, a capacitor 412, and a switch 413.

The switch 411 has a first end connected to a first end of the pickup coil 300 and a second end connected to a first end of the capacitor 412. A second end of the capacitor 412 is connected to the second measurement unit 420.

The switch 413 has a first end connected to the second end of the capacitor 412 and a second end connected to the ground.

As shown in FIG. 4, the second measurement unit 420 includes an operational amplifier 421, a capacitor 422, a switch 423, a switch 424, a capacitor 425, and a resistor 426.

The operational amplifier 421 is an example of an amplifier circuit. A non-inverting input terminal of the operational amplifier 421 is modeled by inputting the low frequency noise component (offset, 1/f noise) of the operational amplifier 421. An inverting input terminal of the operational amplifier 421 is connected to the capacitor 422 and the switch 424. An output terminal of the operational amplifier 421 is connected to the capacitor 425 and the resistor 426.

The capacitor 422 has a first end connected to the second end of the capacitor 412 and a second end connected to the inverting input terminal of the operational amplifier 421.

The switch 423 has a first end connected to the first end of the capacitor 422 and a second end connected to a first end of the capacitor 425.

The switch 424 has a first end connected to the second end of the capacitor 422 and the second end connected to the first end of the capacitor 425.

A second end of the capacitor 425 is connected to the output terminal of the operational amplifier 421 and a first end of the resistor 426. A second end of the resistor 426 is connected to a first end of the pickup coil 300.

Next, operation of the magnetic sensor 1A according to the second embodiment will be described. The operation of the magnetic sensor 1A is roughly divided into three steps (first step, second step, and third step). The magnetic sensor 1A repeats operations in the order of the first step, the second step, and the third step. The first step is performed in the energized state. The second step and the third step are performed in the non-energized state. Note that each switch in the first measurement unit 410 and the second measurement unit 420 may be controlled by a processor (not shown) in the magnetic sensor 1A, or may be controlled by the drive unit 200.

<First Step>

In the energized state, the first measurement unit 410 controls the switch 411 and the switch 413 to be on. Further, in the energized state, the second measurement unit 420 controls the switch 423 to be on, and controls the switch 424 to be off. Accordingly, the first voltage is detected by the capacitor 412 in the energized state. For example, when the sensor head 100 is an amorphous wire, the drive unit 200 generates a rectangular pulse current to energize the amorphous wire. At this time, the first voltage is detected by the capacitor 412 by turning off the switch 411 at an appropriate timing for the peak voltage of the induced voltage (which changes according to the external magnetic field strength to be detected) generated when the rectangular pulse current rises.

<Second Step>

After the first step, the switch 411 is controlled to be off by the first measurement unit 410, and then the sensor head 100 enters a non-energized state. The first measurement unit 410 controls the switch 413 to remain on. Further, the second measurement unit 420 controls the switch 423 to be off, and controls the switch 424 to be on. Accordingly, in the second step, due to the effect of the virtual ground of the operational amplifier 421, a low frequency noise component of the operational amplifier is generated at the inverting input terminal, and is sampled by turning off the switch 413.

Thus, in the second step, by utilizing the effect of the virtual ground of the operational amplifier 421, low frequency noise components such as the 1/f noise of the operational amplifier 421 generated at the inverting input terminal of the operational amplifier 421 and the offset voltage caused by manufacturing variations are detected at the capacitor 422 as a third signal.

<Third Step>

After the second step, the first measurement unit 410 controls the switch 413 to be off, and then controls the switch 411 to be on. Further, the second measurement unit 420 controls the switch 423 to be on, and controls the switch 424 to be off. Accordingly, in the third step, the charge corresponding to the second voltage and the charge corresponding to the low frequency noise component accumulated in the capacitor 422 are subtracted from the charge corresponding to the first voltage accumulated in the capacitor 412, and the remaining charge (fourth signal) is transferred to the capacitor 425 to obtain the corresponding output voltage Vout.

As described above, the magnetic sensor 1A according to the second embodiment has effects similar to those of the first embodiment, and can reduce not only the dynamic offset (low frequency voltage) caused by the parasitic series resistance Rp of the pickup coil 300, but also the low frequency noise component of the operational amplifier 421 in the circuit in the second measurement unit 420.

Third Embodiment

In a third embodiment, a specific second configuration example of the information processing unit 400 of the first embodiment will be described. However, the configuration of the information processing unit 400 of the first embodiment is not limited to the specific configuration described in the third embodiment. In the following description, portions having functions similar to those described in the first embodiment and the second embodiment will be given the same names and reference numerals, and detailed descriptions of the functions will be omitted. However, for convenience of description, the magnetic sensor of the third embodiment is called a "magnetic sensor 1B", and the information processing unit 400 of the third embodiment is called an "information processing unit 400B".

Figure 5:
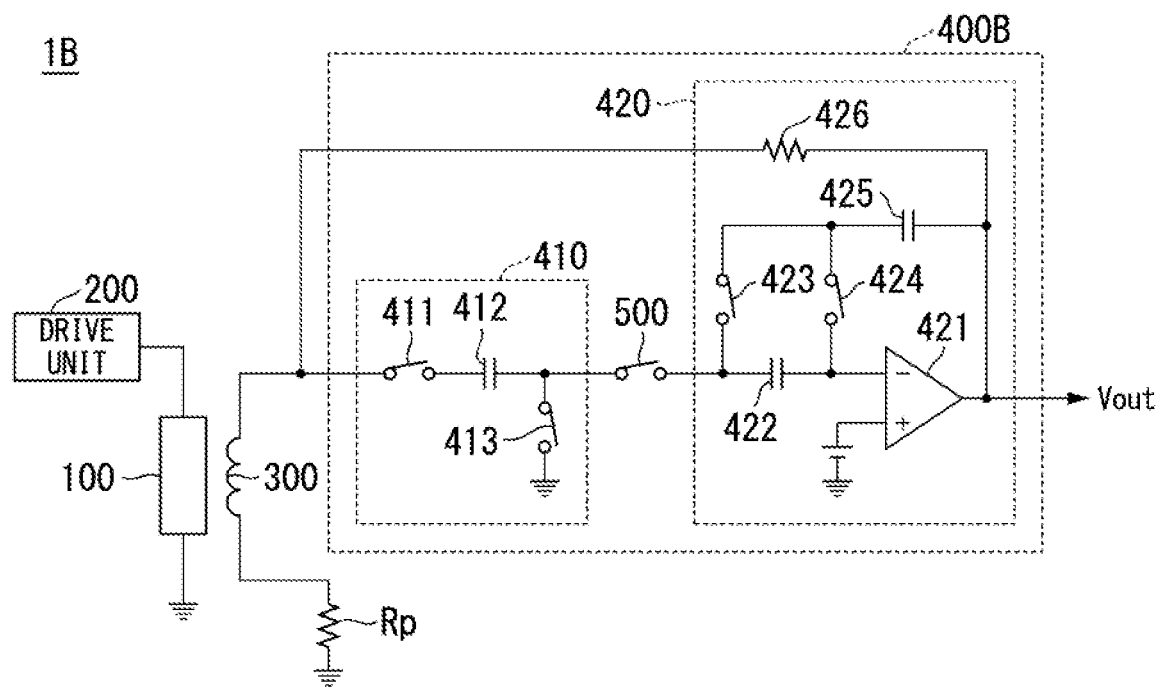
FIG. 5 is a diagram showing a configuration example of a magnetic sensor according to a third embodiment.

FIG. 5 is a diagram showing a configuration example of a magnetic sensor 1B according to the third embodiment. The magnetic sensor 1B includes a sensor head 100, a drive unit 200, a pickup coil 300, and an information processing unit 400B.

The information processing unit 400B includes a first measurement unit 410, a second measurement unit 420, and a switch 500.

The switch 500 can cut off electrical connection between the first measurement unit 410 and the second measurement unit 420. The switch 500 has a first end connected to the second end of the capacitor 412 and the second end connected to the first end of the capacitor 422. The switch 500 cuts off the electrical connection between the first measurement unit 410 and the second measurement unit 420 when the first measurement unit 410 detects the first signal. This makes it possible to reduce the influence of noise from the second measurement unit 420 when the first measurement unit 410 detects the first signal. Note that the switch 500 may be controlled by a processor (not shown) in the magnetic sensor 1B, or may be controlled by the drive unit 200.

Figure 6:
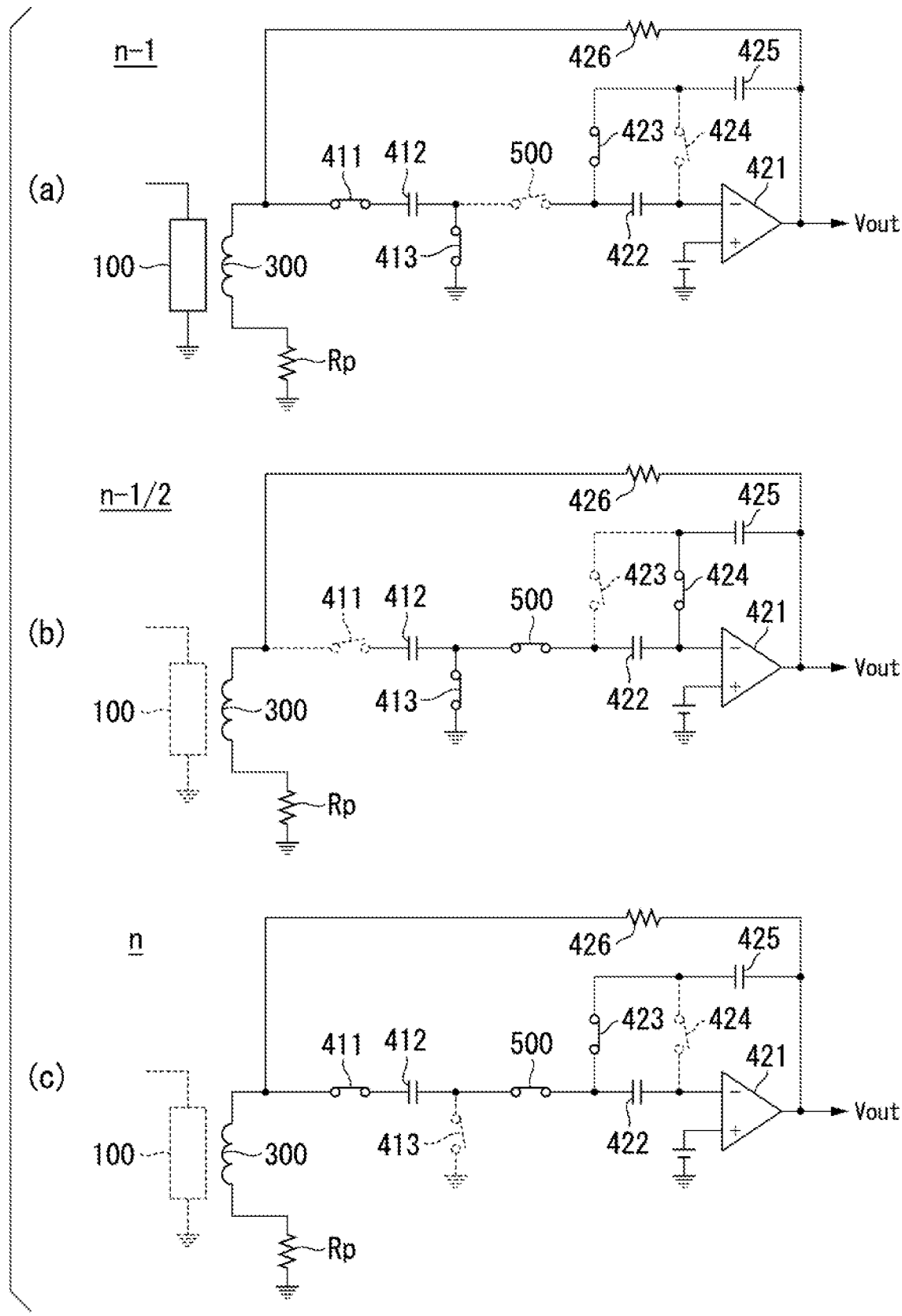
FIG. 6 is a diagram showing a flow of operation of the magnetic sensor according to the third embodiment.

The operation of the magnetic sensor 1B according to the third embodiment will be described below. FIG. 6 is a diagram showing the flow of operation of the magnetic sensor 1B.

The operation of the magnetic sensor 1B according to the third embodiment is roughly divided into three steps (first step, second step, and third step) as in the second embodiment. The magnetic sensor 1B repeats operations in the order of the first step, the second step, and the third step. The first step is performed in the energized state. The second step and the third step are performed in the non-energized state.

<First Step: n-1>

As shown in FIG. 6(a), at time n-1, the sensor head 100 is in an energized state. In the energized state, the first measurement unit 410 controls the switch 411 and the switch 413 to be on in advance. Further, the second measurement unit 420 controls the switch 423 to be on, and controls the switch 424 to be off. Also, the switch 500 is in an off state. Thereby, the first voltage is detected by the capacitor 412 without being affected by noise generated by the second measurement unit 420. For example, when the sensor head 100 is an amorphous wire, the drive unit 200 generates a rectangular pulse current to energize the amorphous wire. At this time, the first voltage is detected by the capacitor 412 by turning off the switch 411 at an appropriate timing for the peak voltage of the induced voltage (which changes according to the external magnetic field strength to be detected) generated when the rectangular pulse current rises.

<Second Step: n-1/2>

As shown in FIG. 6(b), at time n-1/2, after the switch 411 is controlled to be off by the first measurement unit 410, the sensor head 100 changes from the energized state to the non-energized state. The first measurement unit 410 controls the switch 413 to remain on. Further, the second measurement unit 420 controls the switch 423 to be off, and controls the switch 424 to be on. Also, the switch 500 is controlled to be on. As a result, in the second step, due to the effect of the virtual ground of the operational amplifier 421, a low frequency noise component of the operational amplifier is generated at the inverting input terminal, and is sampled by turning off the switch 413. As described above, in the second step, when the inverting input terminal of the operational amplifier 421 is in a state of being virtually grounded, low frequency noise components such as the 1/f noise of the operational amplifier 421 and the offset voltage caused by manufacturing variations are detected at the capacitor 422 as the third signal.

<Third Step: n>

As shown in FIG. 6(c), at time n, the first measurement unit 410 controls the switch 413 to be off, and then controls the switch 411 to be on. Further, the second measurement unit 420 controls the switch 423 to be on, and controls the switch 424 to be off. Also, the switch 500 remains on. Accordingly, the charge corresponding to the second voltage and the charge corresponding to the low frequency noise component accumulated in the capacitor 422 are subtracted from the charge corresponding to the first voltage accumulated in the capacitor 412, and the remaining charge (fourth signal) is transferred to the capacitor 425 and amplified.

As described above, the magnetic sensor 1B according to the third embodiment has effects similar to those of the first embodiment, and can reduce the influence of noise from the operational amplifier 421 of the second measurement unit 420 when detecting the first signal.

Fourth Embodiment

In a fourth embodiment, a specific third configuration example of the information processing unit 400 of the first embodiment will be described. However, the configuration of the information processing unit 400 of the first embodiment is not limited to the specific configuration described in the fourth embodiment. In the following description, portions having functions similar to those described in the first embodiment will be given the same names and reference numerals, and detailed descriptions of the functions will be omitted. However, for convenience of description, the magnetic sensor of the fourth embodiment is called a "magnetic sensor 1C", and the information processing unit 400 of the fourth embodiment is called an "information processing unit 400C".

Figure 7:
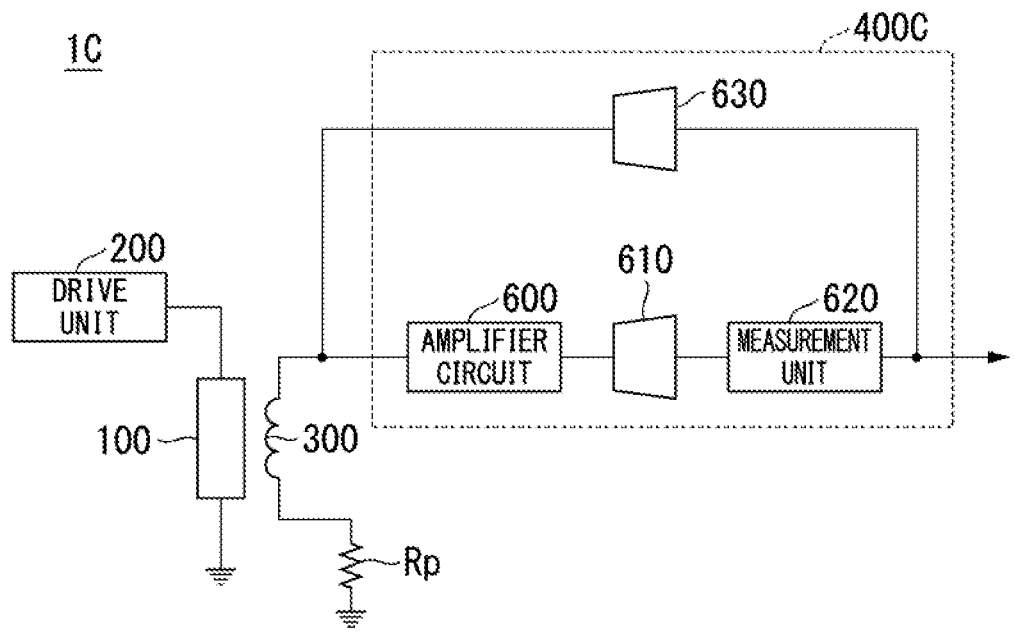
FIG. 7 is a diagram showing a configuration example of a magnetic sensor according to a fourth embodiment.

FIG. 7 is a diagram showing a configuration example of a magnetic sensor 1C according to the fourth embodiment. The magnetic sensor 1C includes a sensor head 100, a drive unit 200, a pickup coil 300, and an information processing unit 400C. The information processing unit 400C includes an amplifier circuit 600, an AD converter 610, a measurement unit 620, and a DA converter 630.

The amplifier circuit 600 is connected to the pickup coil 300. The amplifier circuit 600 amplifies the voltage generated in the pickup coil 300. Then, the amplifier circuit 600 outputs an output signal, which is an amplified signal, to the AD converter 610. For example, the amplifier circuit 600 may include an operational amplifier.

The AD converter 610 converts the output signal from the amplifier circuit 600 into a digital signal. The AD converter 610 then outputs the converted digital signal to the measurement unit 620.

The measurement unit 620 detects a digital signal (hereinafter referred to as a "first digital signal") output from the AD converter 610 when the sensor head 100 is in an energized state. The measurement unit 620 detects a digital signal (hereinafter referred to as a "second digital signal") output from the AD converter 610 when the sensor head 100 is in a non-energized state. The measurement unit 620 then generates a difference signal indicating a difference between the first digital signal and the second digital signal. Note that the measurement unit 620 may communicate with the drive unit 200 and receive information from the drive unit 200 as to whether the current state is a conducting state or a non-conducting state.

The DA converter 630 converts the difference signal generated by the measurement unit 620 into an analog signal and feeds back the analog signal to the pickup coil 300. Accordingly, a current is applied to the pickup coil 300 and a bias magnetic field is generated.

In this way, the magnetic sensor 1C of the fourth embodiment detects the first voltage in the energized state and the second voltage in the non-energized state in the digital domain. Thereby, the magnetic sensor 1C can obtain a voltage obtained by removing the low frequency voltage and the low frequency noise component from the first voltage, that is, the high frequency voltage.

As described above, the magnetic sensor 1C according to the fourth embodiment has effects similar to those of the first embodiment, and can obtain stable accuracy by detecting the induced voltage in the energized state and the induced voltage in the non-energized state in the digital domain and can output the information of the induced voltage corresponding to the external magnetic field as a digital signal to the outside. Therefore, the communication quality for signal transmission can be improved.

Fifth Embodiment

In a fifth embodiment, a specific fourth configuration example of the information processing unit 400 of the first embodiment will be described. However, the configuration of the information processing unit 400 of the first embodiment is not limited to the specific configuration described in the fifth embodiment. In the following description, portions having functions similar to those described in the first embodiment will be given the same names and reference numerals, and detailed descriptions of the functions will be omitted. However, for convenience of description, the magnetic sensor of the fifth embodiment is called a "magnetic sensor 1D", and the information processing unit 400 of the fifth embodiment is called an "information processing unit 400D".

Figure 8:
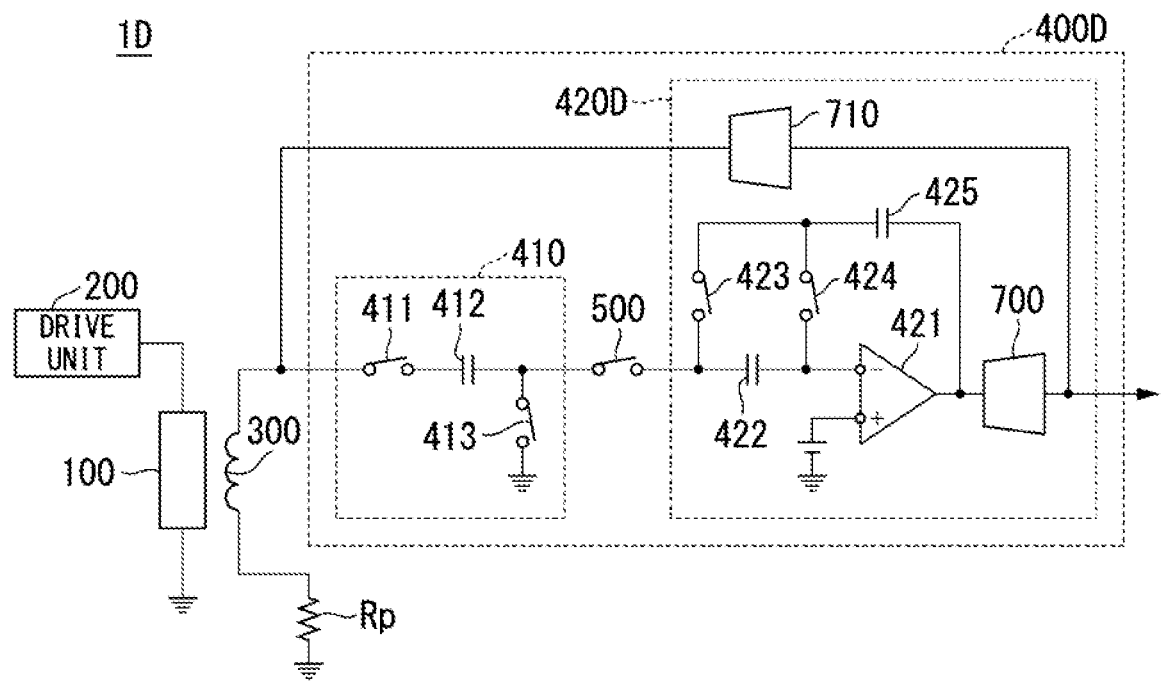
FIG. 8 is a diagram showing a configuration example of a magnetic sensor according to a fifth embodiment.

FIG. 8 is a diagram showing a configuration example of a magnetic sensor 1D according to the fifth embodiment. The magnetic sensor 1D includes a sensor head 100, a drive unit 200, a pickup coil 300, and an information processing unit 400D.

The information processing unit 400D includes a first measurement unit 410 and a second measurement unit 420D.

The second measurement unit 420D is connected to the first measurement unit 410. The second measurement unit 420D has an amplifier circuit and feeds back a current corresponding to an output signal of the amplifier circuit to the pickup coil 300. In addition, the second measurement unit 420D detects a third signal in the non-energized state, and generates a fourth signal indicating a difference between the difference signal output from the first measurement unit 410 and the third signal.

The configuration of the second measurement unit 420D will be described below with reference to FIG. 8.

The second measurement unit 420D includes an operational amplifier 421, a capacitor 422, a switch 423, a switch 424, a capacitor 425, an AD converter 700, and a DA converter 710.

The AD converter 700 is connected to the output terminal of the operational amplifier 421 and converts an output signal output from the output terminal of the operational amplifier 421 into a digital signal. Then, the AD converter 700 outputs the converted digital signal to the outside.

The DA converter 710 converts the digital signal converted by the AD converter 700 into an analog signal and feeds back the analog signal to the pickup coil 300. Accordingly, a current is applied to the pickup coil 300 and a bias magnetic field is generated.

As described above, the magnetic sensor 1D according to the fifth embodiment has effects similar to those of the first embodiment and can output the information of the induced voltage corresponding to the external magnetic field as a digital signal to the outside. Therefore, the communication quality for signal transmission can be improved.

Although the embodiments of the present invention have been described in detail with reference to the drawings, the specific configuration is not limited to these embodiments, and design and the like are included within the scope of the gist of the present invention.

Figure 9:
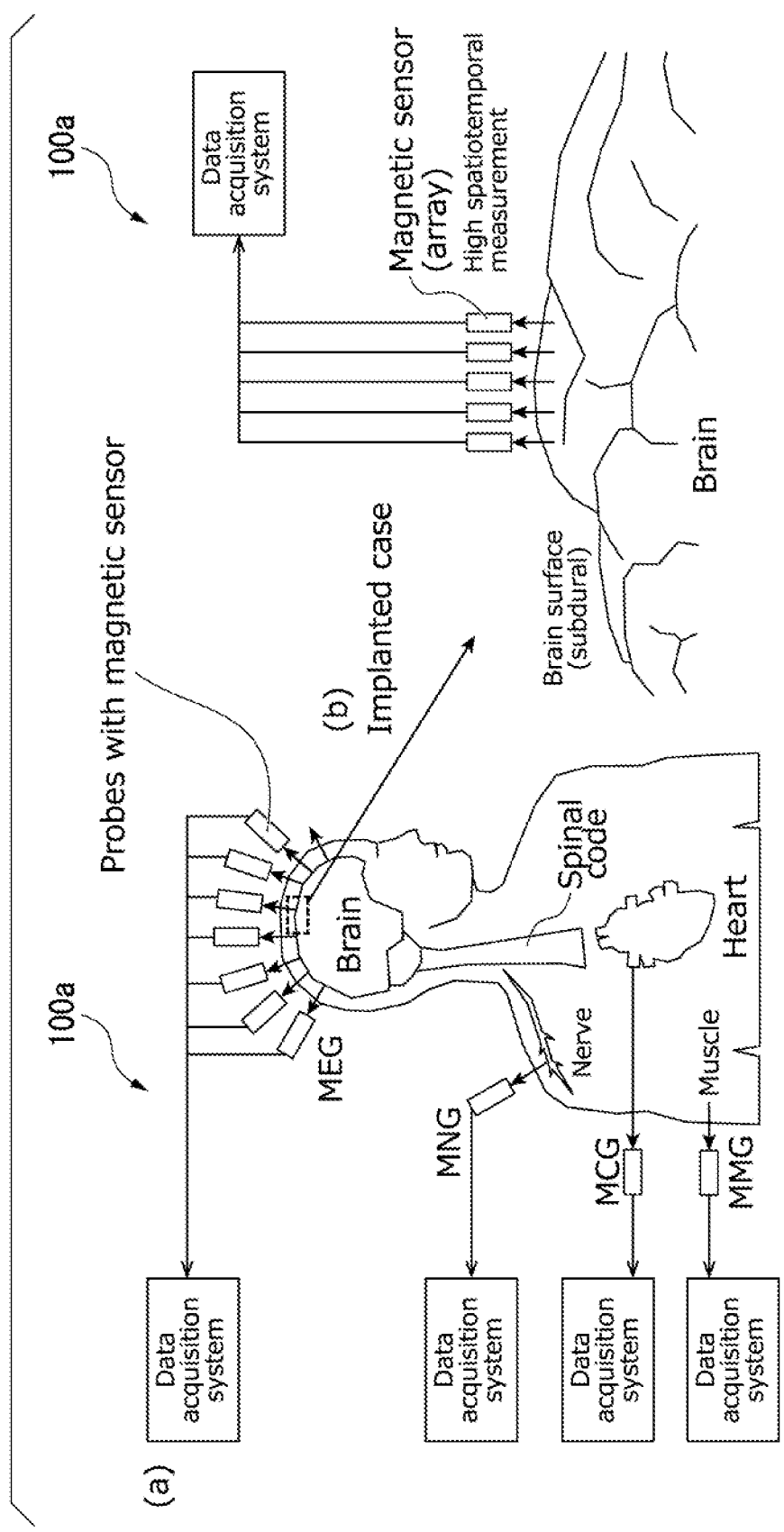
FIG. 9 is a diagram showing a configuration example of a biomagnetic measurement device using the magnetic sensors of the first to fifth embodiments.

By using the magnetic sensor according to any one of the first to fifth embodiments, it is possible to provide a biomagnetic measurement device that performs biomagnetic field measurements such as magnetoencephalography (MEG), magnetoneurography (MNG), magnetocardiography (MCG), magnetomyography (MMG), and bio-embedded brain activity measurement. FIG. 9 is a diagram showing an example of a biomagnetic measurement device 100a according to the present embodiment. FIG. 9(a) shows a configuration example of a biomagnetic measurement device 100a for non-invasive bioinstrumentation such as MEG, MNG, and MMG, and FIG. 9(b) shows a configuration example of a biomagnetic measurement device 100a for implantable (invasive) bioinstrumentation. The biomagnetic measurement device 100a of the present embodiment includes N (N is 1 or more) (channels) magnetic sensors according to any one of the first to fifth embodiments, and includes a biomagnetic measurement unit (data acquisition system) that measures the magnetism emitted by the living body using the output signals from the N magnetic sensors. Since the magnetic sensor of the present embodiment does not require a cooling device such as a SQUID can obtain a signal corresponding to an external magnetic field without using a high-pass filter, it can be miniaturized. Accordingly, there is no need to use a large magnetic sensor head for biomagnetic measurement, and significant miniaturization and cost reduction can be achieved. Further, since the magnetic sensor of the present embodiment can be miniaturized, it is possible to propose not only the biomagnetic measurement device 100a for non-invasive bioinstrumentation as shown in FIG. 9(a), but also a biomagnetic measurement device 100a for implantable (invasive) bioinstrumentation as shown in FIG. 9(b). Each biomagnetic measurement device 100a shown in FIGS. 9(a) and 9(b) may have a configuration in which a probe (array) including a magnetic sensor and a biomagnetic measurement unit are paired. Moreover, in each of the biomagnetic measurement devices 100a shown in FIGS. 9(a) and 9(b), the connection between the probe and the biomagnetic measurement unit may be wired, wireless, or a combination thereof.

Throughout the specification, when a part is referred to as "having" or "including" a component, this does not exclude other components, unless specifically stated to the contrary, and means that other components may be further included.

In addition, the term " . . . unit" described in the specification means a unit that processes at least one function or operation, which may be implemented as hardware or software, or may be implemented in a combination of hardware and software.

REFERENCE SIGNS LIST 1, 1A, 1B, 1C, 1D: Magnetic sensor
100: Sensor head
200: Drive unit
300: Pickup coil
400, 400A, 400B, 400C, 400D: Information processing unit
410: First measurement unit
420: Second measurement unit
600: Amplifier circuit
610: AD converter
620: Measurement unit
630: DA converter

What is claimed is:

1. A magnetic sensor comprising:
a sensor head having a magnetic material;
a drive unit configured to energize the sensor head;
a pickup coil close to the sensor head; and
an information processing unit configured to generate a bias magnetic field by energizing the pickup coil and detect a signal corresponding to a voltage generated in the pickup coil, wherein
the information processing unit generates a difference signal indicating a difference between a first signal corresponding to a voltage generated in the pickup coil when the sensor head is in an energized state and a second signal corresponding to a voltage generated in the pickup coil when the sensor head is in a non-energized state.

2. The magnetic sensor according to claim 1, wherein the information processing unit includes an amplifier circuit, detects a third signal corresponding to a voltage generated at an input terminal using an effect of a virtual ground of the amplifier circuit, generates a fourth signal by subtracting the second signal and the third signal from the first signal, and amplifies the fourth signal with the amplifier circuit.

3. The magnetic sensor according to claim 2, wherein the information processing unit includes
a first measurement unit that detects the first signal in the energized state, detects the second signal in the non-energized state, and generates the difference signal indicating a difference between the first signal and the second signal, and
a second measurement unit that feeds back a current corresponding to an output signal of the amplifier circuit to the pickup coil, detects the third signal in the non-energized state, and generates the fourth signal indicating a difference between the difference signal and the third signal.

4. The magnetic sensor according to claim 3, wherein the information processing unit further includes a switch that cuts off electrical connection between the first measurement unit and the second measurement unit when the first measurement unit detects the first signal.

5. The magnetic sensor according to claim 1, wherein the information processing unit includes
an amplifier circuit that amplifies the voltage generated in the pickup coil,
an AD converter that converts an output signal from the amplifier circuit into a digital signal,
a measurement unit that detects a first digital signal output from the AD converter in the energized state and a second digital signal output from the AD converter in the non-energized state and generates the difference signal indicating a difference between the first digital signal and the second digital signal, and
a DA converter that converts the difference signal generated by the measurement unit into an analog signal and feeds back the analog signal to the pickup coil.

6. The magnetic sensor according to claim 1, wherein the sensor head is an amorphous wire.

7. A biomagnetic measurement device comprising:
the magnetic sensor according to claim 1; and
a biomagnetic measurement unit configured to measure magnetism emitted by a living body using an output signal from the magnetic sensor.

8. The magnetic sensor according to claim 1, wherein the information processing unit negatively feeds back a signal corresponding to the difference signal to the pickup coil.

9. The magnetic sensor according to claim 1, wherein the drive unit controls the sensor head in the energized state and in the non-energized state.

10. The magnetic sensor according to claim 1, wherein the information processing unit amplifies the difference signal.

11. The magnetic sensor according to claim 1, wherein high frequency voltage and low frequency voltage are generated in the pickup coil when the sensor head is in an energized state, and
low frequency voltage is generated in the pickup coil when the sensor head is in an non-energized state.

* * * * *